United States Patent [19]

Brosnan et al.

[11] Patent Number: 4,952,530
[45] Date of Patent: Aug. 28, 1990

[54] DENTAL COMPOSITE MATERIAL AND PROCESS

[75] Inventors: Denis A. Brosnan; Louis J. Colarusso, Jr., both of Solon, Ohio

[73] Assignee: Erico International Corporation, Solon, Ohio

[21] Appl. No.: 278,792

[22] Filed: Dec. 1, 1988

[51] Int. Cl.$^5$ ............................................. C03C 11/00
[52] U.S. Cl. ........................................ 501/39; 501/66; 501/69; 106/35; 65/18.1; 65/18.4; 65/21.4; 65/22
[58] Field of Search ...................... 501/11, 39, 80, 29, 501/66, 64, 81, 84, 99, 46, 69, 8; 433/226, 228.1; 106/35; 65/18.1, 18.4, 21.4, 22

[56] References Cited

U.S. PATENT DOCUMENTS

| 4,381,918 | 5/1983 | Ehrnford | 433/199 |
| 4,392,828 | 7/1983 | Ehrnford | 433/217 |
| 4,503,157 | 3/1985 | Hatahira | 501/1 |
| 4,527,979 | 7/1985 | McLean et al. | 433/228 |
| 4,567,030 | 1/1986 | Yuasa et al. | 423/326 |
| 4,744,759 | 5/1988 | Bowen | 433/228.1 |

OTHER PUBLICATIONS

Jones, "Composites Bite Into New Applications", *Chemical Week* (8/27/86), pp. 43-44.

Primary Examiner—William R. Dixon, Jr.
Assistant Examiner—Deborah Jones
Attorney, Agent, or Firm—Renner, Otto, Boisselle & Sklar

[57] ABSTRACT

A composite suitable for use as dental composite is provided by a glass material having a softening range of at least 10° C. and having a particle size of less than 250 mesh to provide a precursor mix. The precursor mix is mixed with a fugitive pore forming material and a binder to form a pressable mix. The pressable mix is pressed at a pressure in excess of 5,000 pounds per square inch to form a sinterable mix. The sinterable mix is sintered for a period of time sufficient to remove said fugitive pore forming material and to form a sintered mass for crushing to form particles of less than 250 micrometers in size to be incorporated into a dental composite.

9 Claims, 4 Drawing Sheets

MICROSTRUCTURES OF POROUS GLASS SHOWING LARGE OPEN
PORES AND FINE POROSITY NETWORK (100 x)

FIG. I

DENTAL COMPOSITE MATERIAL AND PROCESS

BACKGROUND OF THE INVENTION

This invention relates generally to the art of dental restorations and more particularly to a novel ceramic material for incorporating into a dental composite and a process of producing such material.

Conventionally, human teeth have been treated for decay in dental processes wherein the decayed material is removed by a grinding process and replaced with a material which is generally compatible with the outside enamel and generally nonreactive with the dentine material therebelow. Such material has normally been in the form of an alloy of silver mixed with mercury and referred to as dental amalgam.

Dentists and dental technicians for years have become accustomed to working with such amalgam and have developed the ability to restructure and reshape a tooth surface due to the ability of such amalgam material to respond to molding utilizing dental tools. Such molding is referred to as condensibility and is largely related to the ability of such material to respond to forces applied in directions other than the direction of the applied force. This permits the application of a downward pressure of a dental tool to cause such material to respond laterally and conform to a lateral mold. During the condensation process mercury is forced from the amalgam and removed by mopping such that the mercury content of the amalgam content is actually reduced.

Such dental amalgam, however, has shortcomings with regard to both the cosmetic appearance and durability.

In recent years, a variety of ceramic filled polymer materials have become available which are compatible with the human tooth structure and which may be formed into composites possessing high durability. These materials possess ability to be produced in desired colors. Examples of such polymeric materials are set forth in U.S. Pat. No. 4,744,759 to Bowen which is herein incorporated by reference. The Bowen patent describes not only polymers for use in dental restorations but also a composite material for use in such restoration.

Composite materials involving the use of polymers have been found in general to suffer from the disadvantage of the lack of a formability of the type normally exercised by a dentist during dental restoration. This is generally a lack of the property referred to as condensibility for conventional amalgams. Many composites also have not possessed the wear resistance of conventional amalgams.

Ehrnford in U.S. Pat. Nos. 4,381,918 and 4,392,828 describes processes of producing a material useful in a dental composite utilizing bonded glass fiber matrices. Such fiber matrices have been found to generally possess the characteristics of condensibility required for forming a dental restoration in the conventional manner. The fiber matrix also provided also enhanced wear resistance.

A shortcoming, however, of such glass fiber matrices is the expense thereof associated with very close tolerances required in the manufacturing process.

SUMMARY OF THE INVENTION

It is thus an object of this invention to provide a novel ceramic material for use in a dental composite.

It is a further object of this invention to provide a novel composite material which has the characteristics of condensibility required for dental restorations.

It is a still further and more particular object of this invention to provide a process of producing such a ceramic material which does not require the tolerances associated with prior processes.

These as well as other objects are accomplished by a process for forming a material suitable for incorporation into a dental composite comprising the steps of:

providing a glass material having a softening range of at least 10° C. and having a particle size of less than 250 mesh to provide a precursor mix;

mixing said precursor mix with a fugitive pore forming material and a binder to form a pressable mix;

pressing said pressable mix at a pressure in excess of 5000 pounds per square inch to form a sinterable mix;

sintering said sinterable mix at an elevated temperature for a period of time sufficient to remove said fugitive pore forming material and to form a sintered mass;

crushing said sintered mass to form particles of less than 250 micrometers in size to be incorporated into a dental composite.

DETAILED DESCRIPTION

Figure 1:
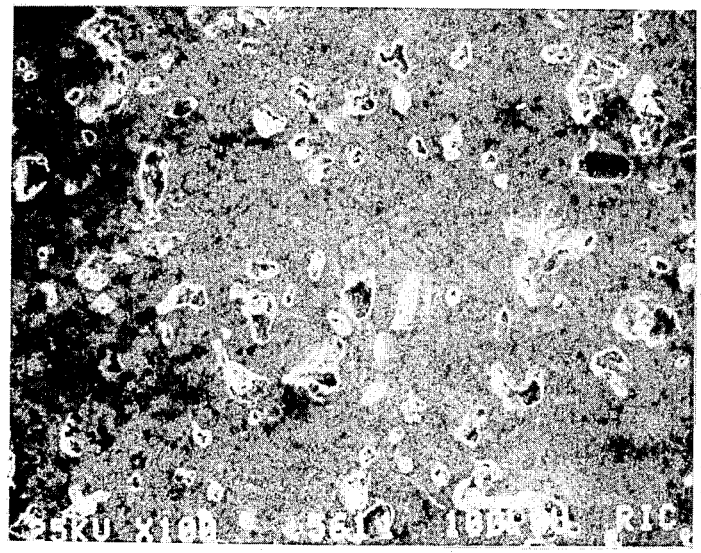
FIG. 1 of the drawings is a photomicrograph of the ceramic material in accordance with this invention prior to crushing at a magnification of 100x.

In accordance of this invention it has been found that a glass material having a softening range in excess of 10° C. may be formed into a material suitable for the formation of dental composites by a unique process. The process provides a material having novel microstructure.

Specifically it has been found that the process of this invention provides a material having a substantial percentage of the porosity within the range of approximately of 1 to 10 micrometers and which may be crushed and sized to form aggregate particles of less than 250 micrometers diameters for use in a composite. Such material characteristics provide for bonding with a bonding polymer in dental restorations as well as possessing the condensibility desirable for forming such material in the restoration process. Surprisingly, the material of this invention when condensed changes its composition in a manner similar to amalgam in that the solids content is increased. This is brought about by the removal of polymeric binder which is forced to the surface during condensation. Various other advantages and features will become apparent from a reading of the following description given with reference to the various figures of drawing.

In accordance with this invention, glass material is formed by the process to be further described. A variety of glass compositions well known to those in the art may be utilized in the process of this invention so long as the softening range thereof is about 10° C. or greater.

As used within this disclosure the term glass is used to mean both glass and glass ceramics which contain crystalline phases. The softening range is thus made with reference to the glass phase of such materials. The broader softening range glasses provide processes that may be carried out economically without the critical temperature controls required in prior art processes. It is thus preferred to have a softening range of about 100° C.

While a preferred glass composition is set forth below such composition is only preferred and is not critical to this invention. The glass composition must, however, be radio opaque to be visible on conventional X-ray equipment.

The initial glass composition is referred to as a precursor mix and is provided at a particle size of less than 250 mesh (U.S. standard) and preferably less than 325 mesh.

The precursor mix is mixed with a fugitive pole forming material which is preferably carbonaceous material at −325 mesh. The fugitive pore forming material is simply a material which burns out during the heating process to leave a pore relic of its prior location behind. Such fugitive materials are well known in the ceramic arts.

A critical aspect of the current invention is that the mixture of the precursor mix and fugitive pore forming material referred to as a pressable mix is pressed at a pressure in excess 5,000 pounds per square inch. It has been found that mere pelletizing at lower pressures provides a material unsatisfactory for the formation of a dental composite. Thus the pressable mix of this invention is formed into disks at pressure in excess of 5,000 pounds per square inch and preferably about 6,000 pounds per square inch and then sintered at a temperature sufficient to remove the fugitive pore forming material.

Preferably the sinterable mix is heated first to a temperature for removal of the fugitive pore forming material and subsequently heated to a higher temperature for sintering. Utilizing the preferred glass composition, it has been found that heating for approximately 6 hours at 700° C. is more than sufficient for removal of the fugitive pore forming material. This is followed by a short sintering within the softening range to provide sintered mass which may be crushed to form aggregates particles of less than 250 micrometers for inclusion into a dental composite. The effective temperatures will of course vary depending on the glass compositions.

Figure 2:
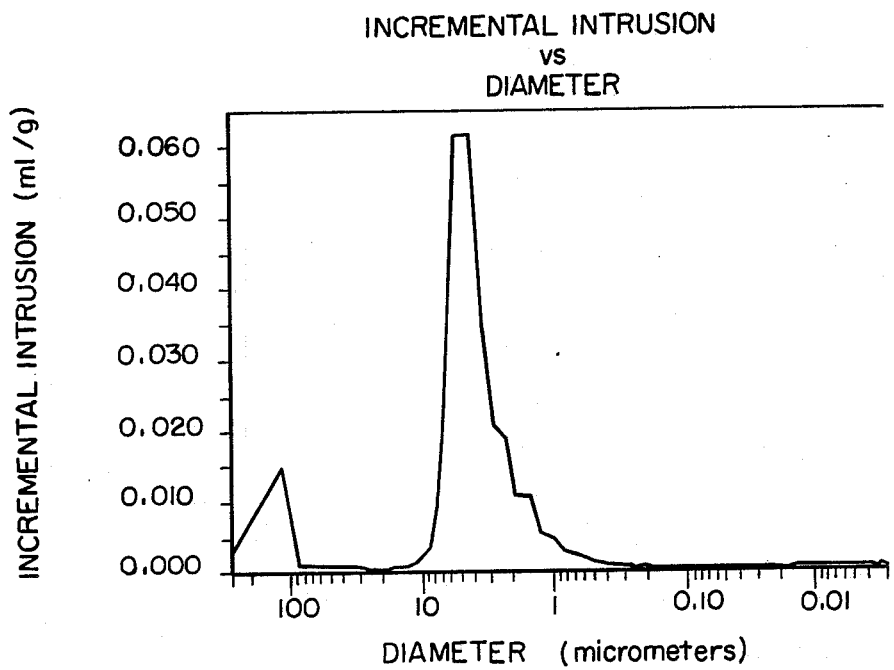
FIG. 2 graphs the pore size distribution of the crushed and sized ceramic material of this invention as it appears from the incremental intrusion technique.

Preferably the composite material after crushing and sizing has a particle size within the range of from about 40 to 250 micrometers. It has been found that such material forms a composite that has the condensibility of dental amalgam. Such composites have been found to load to form a composite with greater than 90 percent solids. This high level of loading is the result of removal of binding polymer during condensation. The material of this invention has a pore size distribution as illustrated in FIGS. 1 and 2 of the drawings of pores mostly within the range of from 1 to 10 micrometers. About 70 percent or greater of the pores are within this range. Such microstructure provides sintered disks that are easily crushed into the preferred aggregate sizes as outlined above. The microstructure of these aggregates bonds with the bonding polymer by surface adhesion and by penetration of the polymer in the porous aggregate. The combination of aggregate size, pore size and degree of porosity provides the condensibility and bonding ability of the composition of this invention.

The very narrow pore size distribution as illustrated in FIG. 2 is uniformly dispersed. The uniformly dispersed porosity is in excess of 30 percent by volume of the material and preferably within the range of 30 to 60 percent to provide both needed porosity and strength. The amount of porosity, the size of the porosity and the dispersion of the porosity together with the particle size of the aggregates all contribute perhaps synergistically to the efficacy of the material of this invention.

As an aid to the further understanding of this invention the following specific examples are given:

EXAMPLES I, II & III

Examples were conducted as generally set forth in Table 1 utilizing a glass of the following composition:

| MATERIAL | WEIGHT PERCENT |
|---|---|
| $SiO_2$ | 57 |
| $Al_2O_3$ | 15 |
| $B_2O_3$ | 14 |
| $SrO$ | 14 |

Precursor mixes were prepared and identified as mixes 18, 42 and 59. Mix 59 is the composition according to this invention with mixes 18 and 42 emphasizing the criticality of process steps of this invention. The glass composition outlined above had a softening point of 990° C. but with a softening range which started at 750° C. The softening range was thus in excess of 200° C.

All samples were mixed from a ground frit of the above composition having the indicated particle size with a carbon fugitive pore forming material in the form of petroleum coke flour. A small amount of a polyvinyl alcohol binder was utilized. Such binders are well known in the art.

TABLE 1

| Composition and Properties Of Porous Glass (Strontium Borosilicate Glass) | | | |
|---|---|---|---|
| COMPOSITION (%) | MIX 18 | MIX 42 | MIX 59 |
| Ground Frit (−325 Mesh) | 85.7 | — | 68.7 |
| Crushed Frit (−35 +70 Mesh) | — | 87.0 | — |
| Pet Coke (−325 Mesh) | 2.9 | 2.2 | 17.2 |
| 5% PVA Solution (Binders) | 11.4 | 10.8 | 14.1 |
| Forming Pressure, lb/in² | Low* | Low | 6,000 |
| Firing Schedule | | | |
| Ramp Rate °C./min. | — | — | 30 |
| Burnout Temp., °C. | — | — | 710 |
| Burnout Time, hrs. | — | — | 8 |
| Sintering Temp, °C. | 800 | 810 | 800 |
| Sintering Time, hrs. | 3 | 4 | 1 |
| Properties | | | |
| Apparent Porosity, % | 37.2 | 38.8 | 42.3 |
| Bulk Density, g/cm³ | 1.5 | 1.5 | 1.4 |
| Diametral Compressive Strength, lb/in² | 181 | 110 | 737 |
| EVALUATION | Condensible but weak; Too much crushing | Condensible but contained non-porous particles | Condensible; Equivalent of amalgam |

*Only sufficient to form pellets (like pelleting)

Mix 18 was only pelletized in an Eirich mixer using sufficient conditions to form pellets. Mix 42 utilized a coarser glass fraction but was still pressed at a low pressure in an Eirich mixer. Mix 59 the mix of this invention was produced by pressing shapes (disks) at a pressure of about 6,000 per square inch. All materials were prepared according to parameters set forth in Table 1 and had the properties set forth therein.

Mix 59, prepared according to the process of this invention had the microstructure as illustrated in FIG. 1 and the pore size distribution as measured by the incremental mercury intrusion technique utilizing a Micrometrics Autopore instrument.

Figure 3:
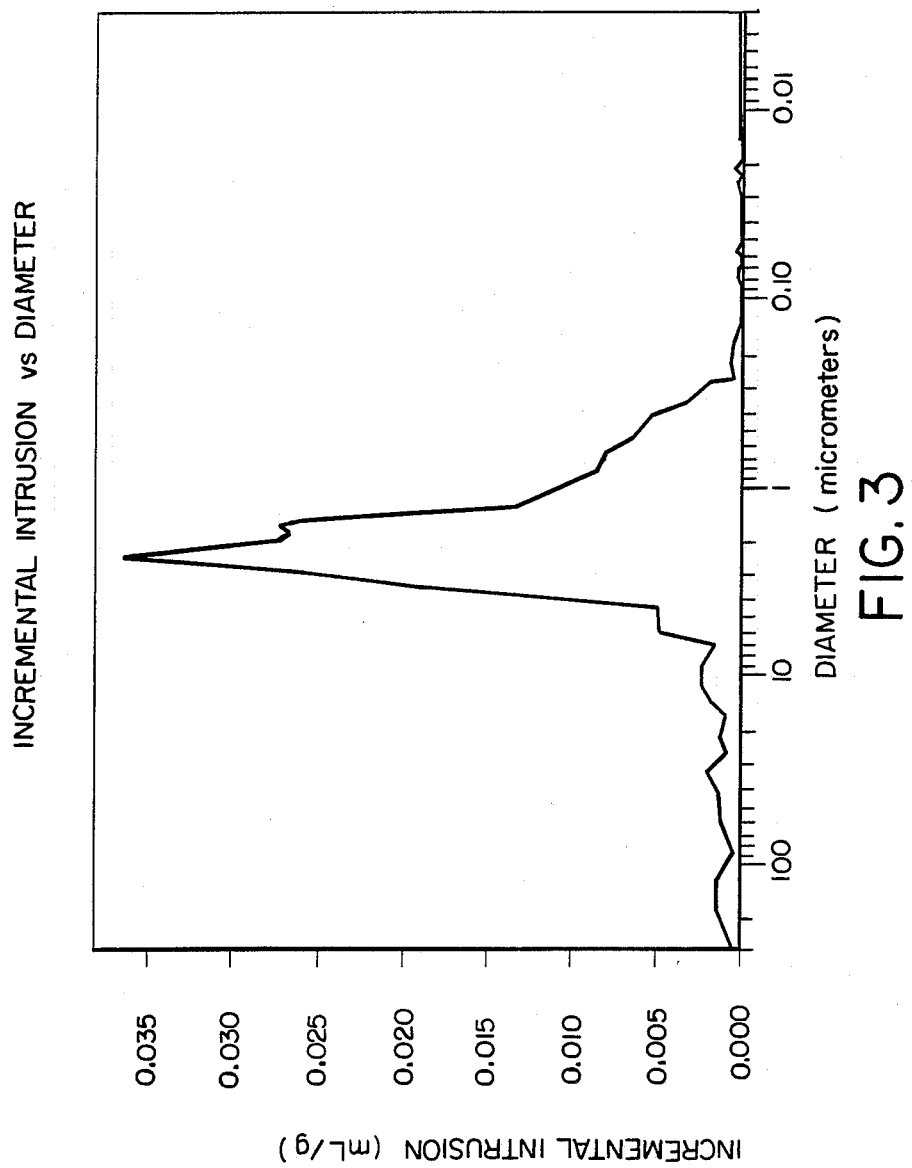
FIGS. 3 and 4 are graphs similar to FIG. 2 of materials not suitable for this invention.
Figure 4:
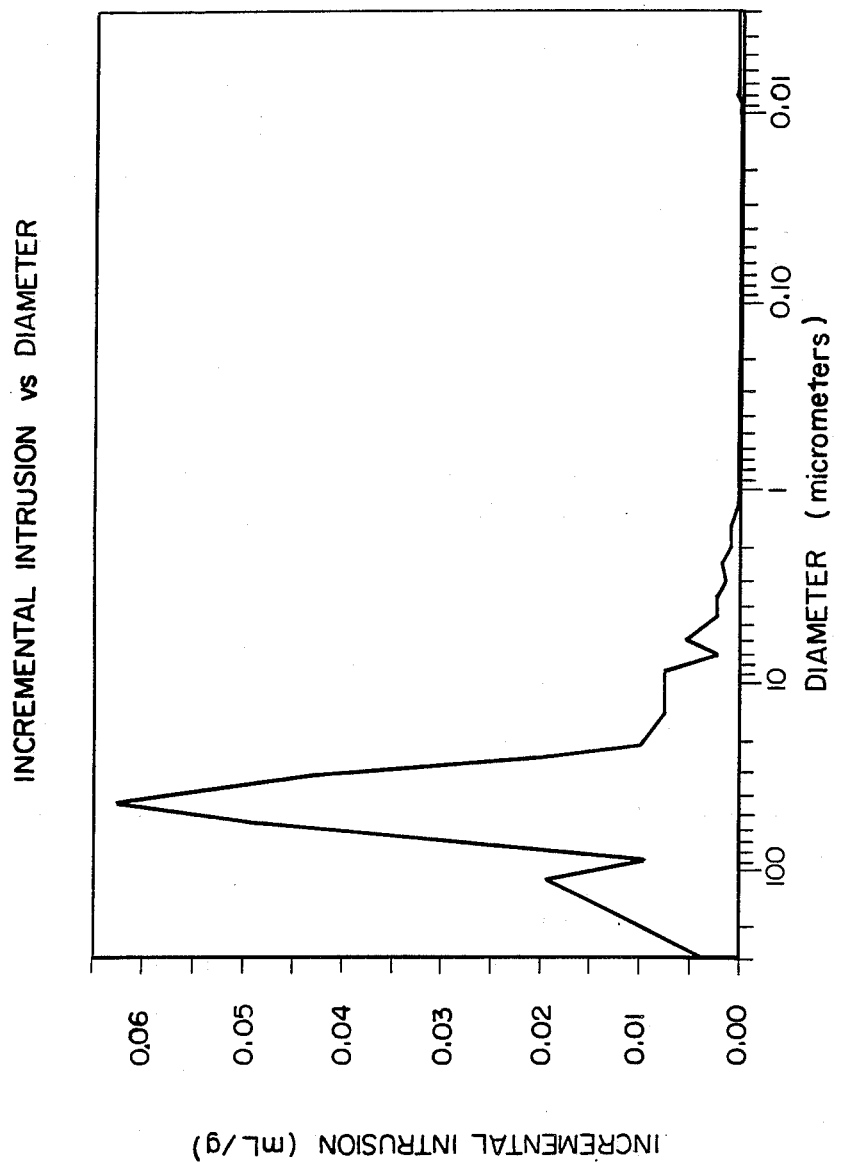

Mix 18 had the pore size distribution illustrated in FIG. 3; while mix 42 had the pore size distribution illustrated in FIG. 4. The material of this invention (mix 59) was found to posses the following attributes:

1. The material is highly condensible using dental instruments to form a composite with greater than about 90 percent solids loading.
2. A microstructure with a bimodal pore size distribution comprised of pore diameters of about 100 micrometers and from 1 to 10 micrometers such that sintered disks easily crushed into an aggregate suitable for use in a dental composite.
3. The very narrow pore size distribution is found in aggregates sized to 40 to 250 micrometers and aggregates are uniformly porous.
4. The composite formed by the material of this invention has substantially the same feel or condensibility as possed by dental amalgam.

EXAMPLE IV

The components of a composite material are the filler aggregate, a microfine non-porous filler for polishability, a coupling agent (to improve the adhesion of the polymer to the ceramic), the polymer (or resinous material), and a catalyst. Various resins and catalysts may be employed with the aggregate. The following mixture was chosen for condensation trials:

| DENTAL COMPOSITE MIXTURE (WEIGHT PERCENT) | |
| --- | --- |
| Mix 59 Aggregate (Sized −250 microns + 44 microns | 69.65 |
| Silane A-174 coupling agent* in acetone | 0.35 |
| Resin solution (70% Bis-GMA, 30% TEGDMA**) | 30.00 |

* Union Carbide Corporation
** Bis-GMA, Freeman Chemical Company TEGMA (triethylene-glycol-dimethacrylate)

The silane was coated onto the Mix 59 aggregate prior to mixing the aggregate with the resin solution. Subsequent to mixing the aggregate with the resin solution, a small amount of photoinitiator or catalyst (benzoin methyl ether) wa added to the composite.

The composite was applied to simulated dental cavities, i.e, holes drilled in an acrylic block, and to holes prepared in human teeth using standard condensation instruments. The prepared fillings were cured using a high intensity dental light source.

The results of these trials were as follows:

1. The material was judged equivalent in condensibility to mercury amalgam by a dental professional in attendance at the trial.
2. Condensed and cured specimens were removed from the acrylic block and found to exhibit greater than 90% ceramic content in the as-placed and cured filling.

It is thus seen that the process of this invention provides a novel ceramic material utilizable to form a novel dental composite.

Such material is produced by a process suitable for mass production not requiring the critical process parameters of the prior art. Such material may be formed into a composite which has the same condensibility as a prior art dental amalgam. As variations of this invention will become apparent to those of skill in the art from a reading of the foregoing description which is exemplary in nature such variations are embodied within the spirit and scope of this invention as defined by the following appended claims:

That which is claimed is:

1. A process for forming a material suitable for incorporation into a dental composite comprising the steps of:
   providing radio opaque a glass material having a softening range of at least 10° C. and having a particle size less than 250 mesh to provide a precursor powder;
   mixing said precursor mix with a fugitive pore forming material and a binder to form a pressable mix;
   pressing said pressable mix at a pressure in excess of 5,000 pounds per square inch to form a sinterable mix;
   sintering said sinterable mix at an elevated temperature for a period of time sufficient to remove said fugitive pore forming material and to form a sintered mass;
   crushing said sintered mass to form particles of less than 250 micrometers in size to be incorporated into a dental composite.

2. The process according to claim 1 wherein said precursor powder is present in an amount of at least 70 percent of said pressable mix.

3. The process according to claim 1 wherein said sintering temperature is within the softening range of said glass material.

4. The process according to claim 3 further including the additional step prior to said step of sintering of removing said fugitive pore forming material at a temperature below said sintering temperature.

5. The process according to claim 1 wherein said fugitive pore forming material is carbonaceous material.

6. The process according to claim 5 wherein said carbonaceous material has a particle size of less than 325 mesh.

7. The process according to claim 1 wherein said precursor powder is a glass comprised of $SiO_2$, $Al_2O_3$, $B_2O_3$, and SrO.

8. A glass composition for inclusion into a dental composite, said composition being radio opaque and being in the form of particles having a size within the range of 50 to 250 micrometers, a porosity in excess of 30 percent by volume with pore sizes within the range of 1 to 10 micrometers for greater than 70% of the pores.

9. The glass composition of claim 8 wherein said porosity is uniformly dispersed.

* * * * *